United States Patent [19]

Young, Jr.

[11] 4,094,307
[45] June 13, 1978

[54] METHOD AND APPARATUS FOR AIDING IN THE ANATOMICAL LOCALIZATION OF DYSFUNCTION IN A BRAIN

[76] Inventor: David N. Young, Jr., 2039 Navahoe Trail, Okemos, Mich. 48864

[21] Appl. No.: 771,683

[22] Filed: Feb. 24, 1977

[51] Int. Cl.² ............................................. A61B 5/04
[52] U.S. Cl. .................................. 128/2.1 B; 128/2 T
[58] Field of Search .................. 128/2.1 B, 2 N, 2 T, 128/2.1 R; 351/6

[56] References Cited

U.S. PATENT DOCUMENTS

| 3,147,373 | 9/1964 | Clynes | 128/2.1 R |
| 3,498,287 | 3/1970 | Ertl | 128/2.1 B |

OTHER PUBLICATIONS

Troelstra, Arne et al., "The Electrical Response of the Human Eye to Sinusoidal Light Stimulation", IEEE Trans on Biomed Engr. VBME22, #5, Sep. 1975, pp. 369-378.
Williams, W. J. et al., "Biological System Transfer--Function Extraction using Swept-Frequency and Correlation Techniques", Med. & Biol. Engr., 1972, v. 10, #5, pp. 609-620.
Marmarelis, P. Z. et al., "White-Noise Analysis of a Neuron Chain: An application of the Wiener Theory" - Science, 1972, #175, pp. 1276-1278.

Primary Examiner—Kyle L. Howell
Assistant Examiner—Francis J. Jaworski
Attorney, Agent, or Firm—Charles P. Padgett, Jr.

[57] ABSTRACT

A method and apparatus for synthesizing a set of optimal sensory stimuli designed to elicit an optimal response for each particular brain electrode location in a subject whose brain is being examined to anatomically localize brain dysfunction. A pseudorandom input signal having the general characteristics of Gaussian white noise is generated and converted into a color video visual stimulus which can be observed by the subject and summed on his retina and associated neural network. A plurality of electrodes are positioned with respect to various different and distinct areas of the brain of the subject to be examined. The subject is shown the color video visual stimulus and the electrical analog response from the electrodes is amplified and stored. The stored analog response signals are cross-correlated with the resynthesized input signal to compute a Wiener kernel representation of the response for each electrode. Portions of the pseudorandom input signal which resulted in insignificant analog responses are masked out so that the subsequent generation of pseudorandom input signals will be bandwidth-limited. The analog responses to the bandwidth-limited visual stimulus are cross-correlated with the resynthesized masked input signal and new Wiener kernel representations are recomputed for each electrode. The recomputed Wiener kernel representations of the response from each electrode are then multiplied in an array processor with the resynthesized bandwidth-limited input signal to compute an optimum visual stimulus for each of the electrodes. These optimum visual stimuli may be subsequently displayed to the subject alone or in conjunction with psychophysical tests to aid in anatomically localizing dysfunction in a brain under examination.

25 Claims, 4 Drawing Figures

METHOD AND APPARATUS FOR AIDING IN THE ANATOMICAL LOCALIZATION OF DYSFUNCTION IN A BRAIN

BACKGROUND OF THE INVENTION

The present invention relates to a method and apparatus for anatomically localizing dysfunction in a particular sensory system of the brain and more particularly to a method and apparatus for synthesizing a set of optimal sensory stimuli each designed to elicit an optimal response for a particular electrode location in a subject whose brain is being examined to anatomically localize dysfunction within the examined portion of the brain.

The present invention is particularly useful in applications wherein a dysfunction in a porton of a person's brain cannot be cured by pharmaceuticals, thereby rendering surgical removal the only viable alternative. It is desirable in such cases to remove only that portion of the brain which gives rise to the problem. Otherwise, various unaffected visual, auditory, vestibular and other brain functions may be unnecessarily lost.

The prior art teaches that the output of a non-linear system may be analyzed if the input can be assumed to possess the general characteristics of Gaussian white noise. Furthermore, the nature of such non-linear systems may be analyzed by representing the system in terms of Wiener kernals obtained by cross-correlation techniques.

Researchers are now attempting to utilize various complex mathematical representations to characterize the output of biological systems, but none of the research is directed toward synthesizing an optimal sensory stimuli and then utilizing the optimal sensory stimuli as an aid in anatomically locating dysfunction in the visual, auditory or vestibular portion of a brain under examination.

The method and apparatus of the present invention aids in determining the precise anatomical localization of a dysfunction in a particular area of the human brain thereby rendering surgery much more precise and exact and minimizing the chance of unnecessarily removing undamaged portions of the brain in the process.

The present invention goes far beyond anything heretofore attempted in the prior art and provides a method and apparatus for significantly aiding in the anatomical localization of dysfunction in the human sensory system. Information obtained by use of the synthesized optimal sensory stimuli of the present invention may be used for localization purposes, for diagnostic and verification purposes, or for obtaining further research information concerning sensory systems and their responses to various stimuli.

BRIEF SUMMARY OF THE INVENTION

The present invention teaches a method for determining the specific anatomical localization of a dysfunction in a portion of the sensory system of a brain. The method includes placing a plurality of electrodes at different discrete physical areas of the subject's brain under examination. A sensory stimulus having the general characteristics of Gaussian white noise is generated and the sensory stimulus is displayed to the subject. The electrical analog signals produced in the brain in response to the presentation of the sensory stimulus to the subject are amplified and recorded. The sensory stimulus is resynthesized and cross-correlated with the recorded analog response signal for each placed electrode to obtain a Wiener kernel representation thereof. The bandwidth of the sensory stimulus is then limited by masking out those portions which produce insignificant responses and the bandwidth-limited sensory stimulus is then presented to the subject. The electrical analog response from each of the electrodes is amplified and recorded. The bandwidth-limited sensory stimulus is resynthesized and cross-correlated with the stored analog response of the signals to recompute a Wiener kernel representation thereof. A set of optimal, kerneldefined sensory stimuli are then defined, one for each of the placed electrodes, by multiplying the resynthesized bandwidth-limited sensory stimulus by the recomputed Wiener kernel representations. The optimal, kernel-defined sensory stimuli may be presented to the subject and the most neurophysiologically significant responses studied to analyze the nature of the disorder and to aid in isolating the anatomical location of the dysfunction, if any exists, within the area of the brain under examination.

In the preferred embodiment of the present invention, the visual portion of the brain was examined to anatomically localize dysfunction causing temporal lobe epilepsy. The stimulus, therefore, was visual and at least the first, second and third order Wiener kernels were computed for the purpose of representing the output from the individual electrodes.

The system of the present invention provides for the synthesis of a set of "n" discrete optimal visual stimuli for each different and distinct brain area being examined for use in determining the anatomical localization of brain dysfunction. The system includes a means for generating a pseudorandom input signal having the general characteristics of Gaussian white noise. A means responsive to the input signal is provided for displaying a color video visual stimulus representation thereof so that the visual stimulus may be summed on the retina and associated neural network of the subject whose brain is being examined.

A plurality of "n" individual electrodes are provided and one of the electrodes is disposed adjacent each of the different and distinct brain areas to be examined. The electrodes provide for monitoring the electrical spikes and slow potential responses produced in those brain areas when the subject observes the displayed visual stimulus. An "n" channel amplifier is provided and one of each of the channels is connected to each of the electrodes for amplifying the electrical analog response signals therefrom. The amplified output of each of the channels of the amplifier are stored. Computational means responsive to the storage means and the input signal generating means is provided for crosscorrelating a resynthesized input signal with the stored electrical analog response to compute a Wiener kernel representation of the response from each of the electrodes and for determining which portions of the input signal give rise to insignificant responses.

A means responsive to the determination of which portions of the input signal were responsible for the insignificant responses masks out the subsequent generation thereof so as to limit the bandwidth of any subsequently generated input signals. The computational means is responsive to the resynthesized, subsequently regenerated, bandwidthlimited input signal and to the subsequently stored electrical analog response signals measured by the electrodes in response to the subject's observation of the displayed, bandwidth-limited visual stimulus for cross-correlating to obtain a recomputed Wiener kernal representation of the output of the electrodes.

An array processor is provided for multiplying the recomputed Wiener kernel representation of the output of each of the electrodes and the resynthesized bandwidth-limited input signals to produce an optimal input signal for each of the "n" electrodes which can be supplied to the display means for displaying an optimal visual stimulus for testing each of the different and distinct brain areas being examined as an aid in anatomically localizing brain dysfunction.

The method and apparatus of the present invention provides a relatively positive means for anatomically localizing dysfunction in the brain. The present invention insures that large usable portions of the brain are not removed in order to eliminate a brain dysfunction whose cause is, in fact, isolated to a small brain area.

The method and apparatus of the present invention will allow far greater physical and psychological studies, tests and analyses to be run to increase the present day knowledge of the sensory systems of the brain and problems arising from dysfunction therein.

The method and apparatus of the present invention could be used, for example, to test potential candidates for helicopter pilot training programs in order to screen out or treat actual epileptics and those having a propensity theretowards.

Other advantages and meritorious features of the present invention will be more fully understood from the following detailed description of the drawings in the preferred embodiment, the appended Claims and the drawings, which are briefly described hereinbelow.

DESCRIPTION OF THE PREFERRED EMBODIMENT

Figure 1:
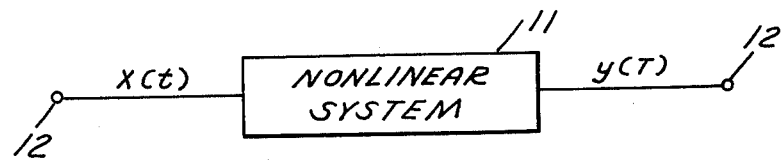
FIG. 1 is a block diagram representing the response of a nonlinear system to a Gaussian white noise input.

FIG. 1 shows a block diagram representation of an unknown nonlinear system 11 whose input 12 has been supplied with an input signal x(t) which has the general characteristics of Gaussian white noise. The output y(t) of the system 11 is taken from output terminal 13 and may be represented by the orthogonal expansion $$y(t) = \sum_{n=1}^{\infty} G_n[h_n, x(t)]$$

in which $\{h_n\}$ is a set of kernels of the non-linear system 11 and $\{G_n\}$ is a complete set of orthogonal functions.

As taught by Lee, Y. W. and Schertzen, N. in their article entitled "Measurement of the Kernals of a Non-Linear System by Cross-Correlation" which was published in the *Massachusetts Institute of Technology Research Laboratory Electronics Quarterly Progress Report,* pp. 118–130 (1961) the kernels defining a non-linear system may be calculated by cross-correlation techniques which avoid orthogonal expansions by using an adjustable delay time or time lag "$\sigma$".

Figure 2:
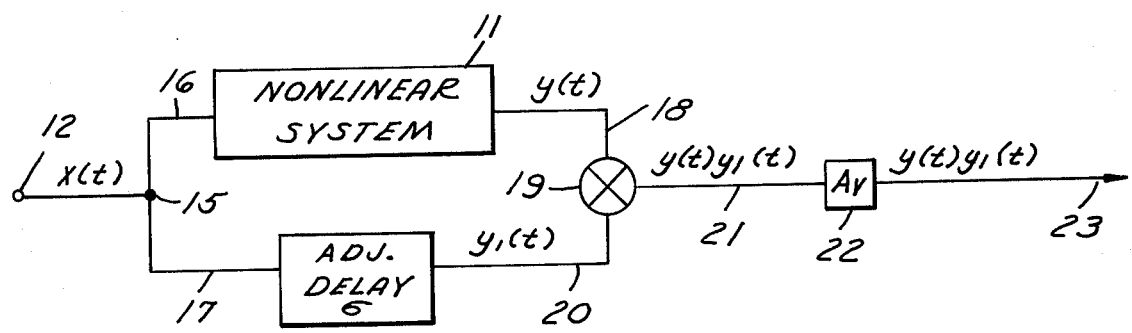
FIG. 2 is a block diagram illustrating the characterization of the non-linear system in terms of Wiener kernel representations thereof by use of variable delay circuits.

Referring to FIG. 2, an adjustable delay circuit 14 is connected in parallel with the non-linear system 11. The input signal $x(t)$ is a white Gaussian process whose power density spectrum is $K/2\pi$ watts per second which may be thought of as an autocorrelation function. The input signal $x(t)$ is supplied to the input terminal 12 and then to input node 15. It then passes via lead 16 to the input of the non-linear system 11 and via lead 17 to the input of an adjustable time delay circuit 14. The output $y(t)$ of the non-linear system 11 is supplied via lead 18 to a multiplier 19 while the output $y_1(t)$ of the adjustable delay 14 is supplied via lead 20 to the multiplier 19. The output of the multiplier 19 is supplied via lead 21 to an averaging network 22 and the time average of the output $\overline{y(t)y_1(t)}$ is taken from the output of the averaging network 22 and supplied to a system output terminal 23.

The output $y(t)$ of the adjustable delay circuit 14 may be expressed by the equation $y_1(t) = x(t - \sigma)$ which can be written alternatively as $$y_1(t) = \int_{-\infty}^{\infty} u(\lambda - \sigma)x(t - \lambda)d\lambda$$

which is a functional of the first degree which we shall define as a one dimensional-delay white Gaussian process. In a similar manner, we can form a white Gaussian process with a two-dimensional delay, with a three-dimensional delay and with a "n" dimensional delay, as desired. The use of these functionals in the measurement of isolated kernels is standard practice, but various complex series expansions are normally used to define the kernels.

According to the teachings of Lee and Schertzen, the non-linear system 11 can be characterized by a set of kernels $\{h_n\}$ of the non-linear system 11. By applying the Gaussian input signal $x(t)$ to the input of the nonlinear system 11 and the adjustable delay network 14, then multiplying their outputs and averaging the product, we find that $$\overline{y(t)y_1(t)} = \left\{ \sum_{n=1}^{\infty} G_n[h_n, x(t)] \right\} \times t - \sigma)$$

Since $x(t - \sigma)$ is a functional of the first degree, the functionals $G_n$ for $n > 1$ are orthogonal to $x(t - \sigma)$. Since $G_1$ can be expressed as $$G_1[h_1, x(t)] = \int_{-\infty}^{\infty} h_1(\lambda_1)x(t - \lambda_1)d\lambda_1$$

then the time average of the product of the cross-correlation may be expressed by the equation $$\overline{y(t)y_1(t)} = \int_{-\infty}^{\infty} h_1(\lambda_1)Ku(\sigma - \lambda_1)d\lambda_1 = kh_1(\sigma)$$

Using this equation, we can determine the first order kernel of the non-linear system 11

$$h_1(\sigma_1) = \frac{1}{k} \overline{y(t)y_1(t)}$$

Similarly, a two-dimensional delay circuit may be used and the system outputs cross-correlated to obtain the second order kernel of the unknown non-linear system 11 which is given by the equation $$h_2(\sigma_1,\sigma_2) = \frac{1}{2k^2} \overline{y(t)y_2(t)}$$

Similarly, a third adjustable delay may be added to provide a three-dimensional delay circuit and the outputs cross-correlated to define the third-order kernel of the non-linear system 11 in terms of the cross-correlation as $$h_3(\sigma_1,\sigma_2,\sigma_3) = \frac{1}{6k^3} \overline{y(t)y_3(t)}$$

for $\sigma_1 \neq \sigma_2 \neq \sigma_3$.

Higher ordered kernels may also be determined for further definition or characterization of the system. For example, the nth-order kernel may be shown to be given by the equation $$h_n(\sigma_1,\sigma_2,\ldots \sigma_n) = \frac{1}{n!k^n} \overline{y(t)y_n(t)}$$

except when, for $n > 2$, two or more of the $\sigma$'s are equal.

The above method of measurement of the kernels used to characterize the non-linear system 11 is extremely simple when compared to the complex mathematical expansion methods previously used. Digital computation and tape recording become possible with the application of the expression of the kernels by the present method. In theory, it should be possible to characterize any non-linear system by determining its kernels of all orders, by recording the white Gaussian process that is fed into the non-linear system, and then cross-correlating the recorded white Gaussian process with the system output for the number of delays desired.

Figure 3:
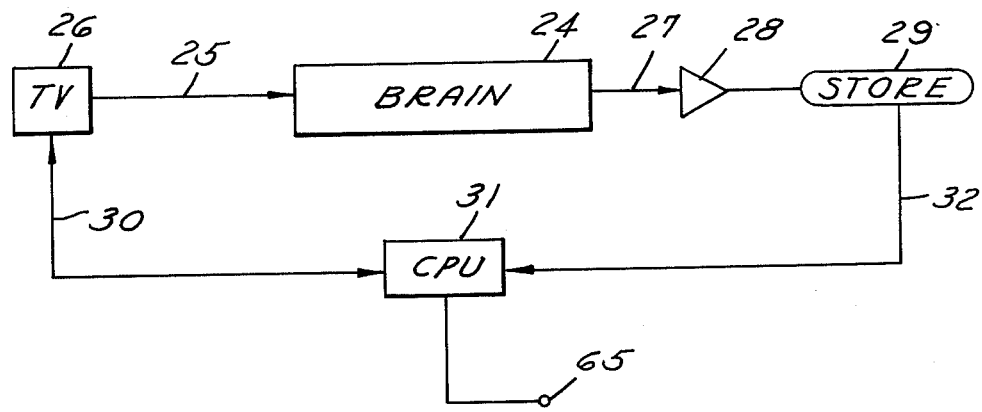
FIG. 3 is a block diagram generalization of the theory of the system of FIG. 1 as applied in the present invention.

FIG. 3 illustrates a block diagram showing how the above theory is applied in the present invention. The non-linear system to be analyzed is represented by the block 24 which stands for the human brain or various portions thereof. A sensory stimulus signal is supplied to the input 25 of the brain 24 by means of a stimulus generator such as the color television video monitor of block 26. The output of the brain 24 is taken via lead 27 to an amplifier 28 whose output is then stored as represented by block 29.

A reproduced or resynthesized sensory stimulus is supplied via lead 30 back to the central processor unit 31 while the stored (delayed) response the signal is provided from the storage block 29 to the central processor unit *pr* CPU 31 by lead 32. The cross-correlated output of the central processor unit 31 may then be taken from the output terminal 65 and used to synthesize a set of optimal sensory stimuli to be used for further testing purposes. Further, the output terminal 65 could be connected to various types of prior art output means such as a strip printer or the like.

Figure 4:
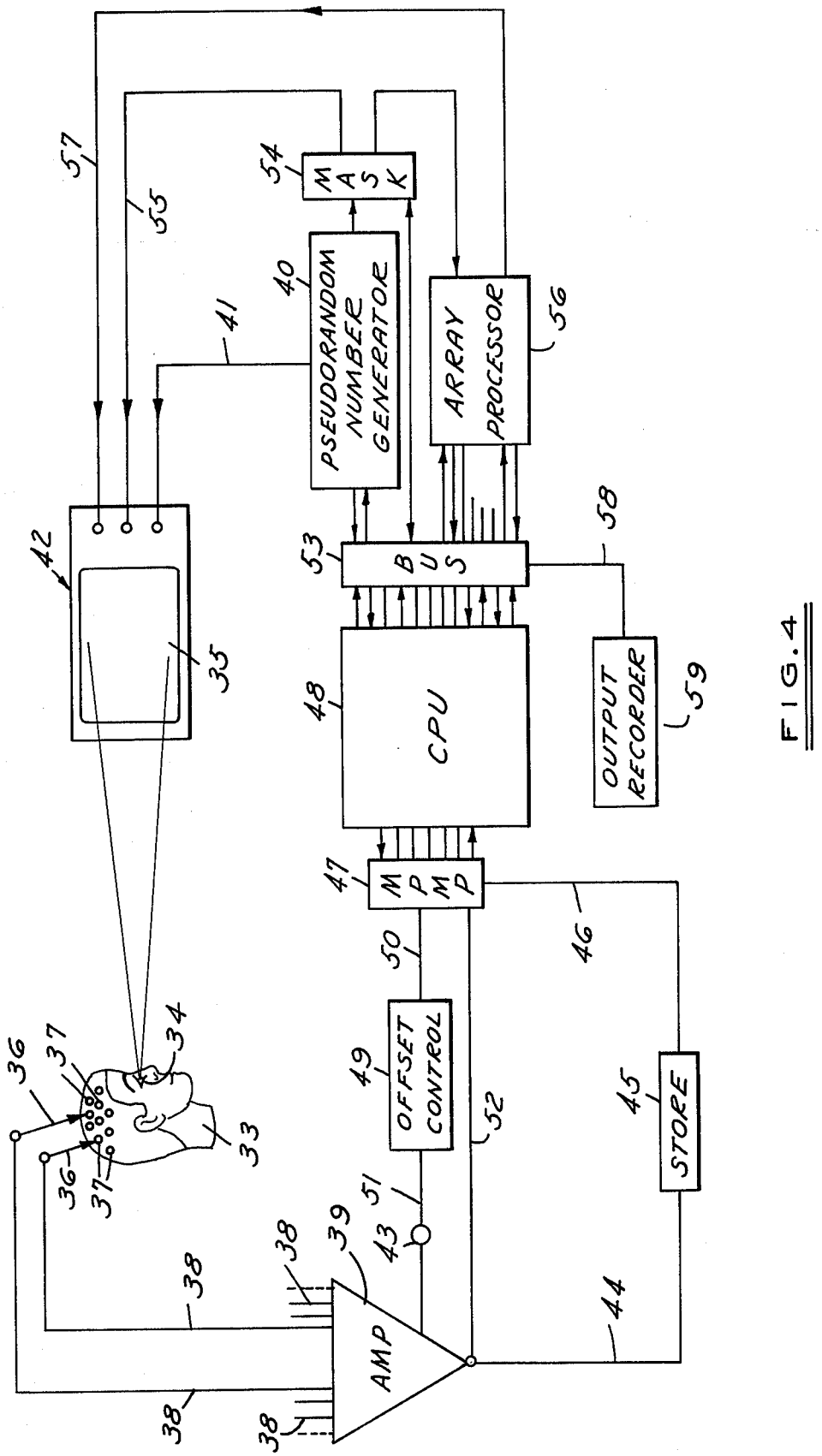
FIG. 4 is a schematic block diagram illustrating the system of the present invention as used to implement the method thereof.

The method and apparatus of the preferred embodiment of the present invention will be described with reference to the block diagram of FIG. 4. It will be understood that while the description specifically refers to an attempt to localize dysfunction in temperal lobe epilepsy, any type of brain dysfunction or syndrome may be isolated by the present technique and various other sensory areas of the brain including the auditory system and the vestibular system could also be utilized. For example, instead of the generation of a visual stimulus when the visual sensory system is being examined, sound patterns could be generated for studying the auditory sensory system and a centrifuge device could be used for studying the vestibular sensory system.

In the preferred embodiment of the present invention, a method and apparatus is provided for synthesizing a set of optimal sensory stimuli, e.g., visual stimuli in the preferred embodiment, each designed to elicit an optimal response for each particular brain electrode location in a subject whose brain is being examined to anatomically localize dysfunction in, for example, temporal lobe epilepsy. The subject 33 is positioned so that he has his eyes 34 focused on a video display screen 35. A plurality of "$n$" electrodes 36 are placed at various different and distinct anatomical locations about that portion of the subject's brain which is under examination. A plurality of leads 38 connect the electrodes 36 to individual inputs of a "$n$" channel amplifier 39 to be described hereinafter.

The electrodes 36 may be conventional surface electrodes which are selectively arranged at predetermined locations about the surface of the subject's skull to record electrical analog response signals coming from the brain area immediately thereunder. Or, in the alternative, they could be surgically implanted into the specific brain areas to be studied, as desired.

In the preferred embodiment of the present invention, a pseudorandom number generator 40 is provided for generating an input signal having the general characteristics of Gaussian white noise. The circuitry of the pseudorandom number generator 40 may include a concatenation of a series of shift registers connected to generate an endless sequence of binary digits. A hierarchial network may be used to pick off a random sequence of the binary digits and this random sequence could be used as the input signal. The random sequence would be multiplexed into complete words, one byte per color and one byte to key the synchronization circuitry of a color video monitor system 41. The arrangement of the shift registers of the pseudorandom number generator 40 would be such that given a repeated starting state, the output sequence would be repeated for resynthesis purposes. The output signal from the pseudorandom number generator 40 is supplied via data path 41 to the color video monitor or digitally-controlled color television system 42. The video system 42 is adapted so that it is responsive to a digital input signal for generating and displaying a color video signal or visual stimulus on the screen 35, the stimulus being a visual representation of the input signal from the pseudorandom number generator 40 and having, therefore, the general characteristics of Gaussian white noise.

The subject 33 has his eyes 34 focused on the screen 35 of the video system 42. As he observes the changing visual stimuli presented on the screen 35, the visual stimuli is summed on his retina and associated neural networks. The visual system of his brain will respond to the visual stimulus to generate various electrical spike and slow potential waveforms, as known in the art. The electrodes 36 will pick up or measure the electrical analog response of those portions of the brain immediately adjacent thereto and will transmit these electrical analog signals back to the amplifier 39 via leads 38.

The amplifier 39 could, for example, be some modification of existing Grass amplifiers commonly used in EEG work or, could be modified differential amplifiers such as the type 7A22 model currently manufactured by Tektronix. The amplifier 39 would preferably have a very high input impedance so as to be able to handle both the electrical spikes and the slow potential waveforms from the subject's brain and would include "n" channels, one for each of the "n" electrodes 36 placed with respect to the subject's brain.

The amplifier 39 would also include a DC offset input 43 which is coupled to a front end amplifier design to allow for the compensation of large potential variances while maintaining the high input impedance and low amplifier noise. It is necessary to compensate for great potential variance since, for implanted electrodes 36, a considerable build-up of electric potential may occur adjacent the electrode which must be compensated for in order to be able to examine changes in the slow potentials.

The "n" channels of the amplifier 39 are supplied via data path 44 to a storage media 45, such as an analog magnetic tape having "n" channels thereon for recordation. The recorded outputs may be supplied via data path 46 to the microprogramable microprocessor 47 which serves as the input to the central processing unit or CPU 48. The CPU 48 could be, for example, a SEL 32/55 computer which is manufactured by Systems Engineering Laboratories. The microprogramable microprocessor input 47 will serve as an analog-to-digital converter for the recorded outputs from the storage media 45 for entry in to the CPU 48.

The CPU 48, by or through the MPMP 47, may digitally control the generation of a compensation signal via the offset control circuitry of block 49. The digital command may be passed from the MPMP 47 to the offset control circuitry 49 via data path 50 and the compensation signal may be supplied via data path 51 to the DC offset input 43 for compensating the amplifier 39 for great potential variances. Data path 52 indicates that the amplifier analog response signals may be supplied directly to the CPU 48 without the need for recording them in the storage media 45, if desired. This could be done if it were desirable to directly record as well as or instead of storing the amplified analog signals.

The initial visual stimulus and/or the pseudorandom input signal representative thereof may be resynthesized by the pseudorandom number generator 40 and supplied via the data bus 53 back to the CPU 48. The CPU 48 can perform the multiplication necessary to crosscorrelate the resynthesized, broadband, visual stimulus-generating digital signal from the pseudorandom number generator 40 with the recorded analog response signal from the storage media 45 for each placed electrode 36 to obtain a Wiener kernel representation of the system response. In the preferred embodiment of the present invention, at least the first, second and third order Wiener kernels are computed for representing the system, but it will be realized that any number of orders of Wiener kernels can be used to represent the system, depending on the accuracy required. The greater the number of orders of the kernels computed to represent the system, the more accurate the representation. In the preferred embodiment, the pseudorandom number generator 40 actually resynthesizes or regenerates the pseudorandom number sequence which generated the original broadband visual stimulus but the sequence could also be recorded and then played back instead of regenerating the sequence, if desired.

The products the cross-correlation are examined in the CPU 48 to determine which, if any, of the cross-correlation products have small absolute values. The products which result from insignificant electrical analog response signals from the electrodes 36 are determines and those portions of the binary sequence of the input signal from the pseudorandom number generator 40 which gave rise to those insignificant responses are then masked out of the pseudorandom number generator 40 by the CPU-controlled masking network 54 so that the future generation of the pseudorandom binary sequence making up the input signal will be bandwidth-limited and will not include those portions which previously gave rise to the insignificant electrical responses in the brain. The masked output of the pseudorandom number generator 40 will exit the masking network 54 via circuit path 55 which feeds the bandwidth-limited or masked digital input signal to the color video monitor system 42. The system 42 will convert the bandwidth-limited digital input signal into a bandwidth-limited color video visual stimulus which is displayed on the screen 35 and summed on the retina and associated neural network of the subject 33.

The electrical analog responses measured by the electrodes 36 in the brain locations 37 are passed via leads 38 to the amplifier 39. The amplified outputs are then passed via paths 44 to the storage media 45 and recorded on individual storage channels. The bandwidth-limited input signal and/or visual stimulus resulting therefrom is resynthesized by the pseudorandom number generator 40 and mask 54 and fed via bus 53 back to the CPU 48 to be crosscorrelated with the subsequently stored analog responses which were generated in response to the bandwidth-limited visual stimulus on the screen 35. The crosscorrelation results in recomputing at least the first, second and third order Wiener kernel representations of the system. Since each Wiener kernel set characterizes the electrical analog response from one of the electrodes 36, and hence from one specific area of the subject's brain under examination, we have a different kernel-defined representation of the response recorded by each of the electrodes 36.

An optimal kernel-defined visual stimulus "Λ" can then be synthesized or generated for each of the electrodes or areas of the brain under examination. The optimal kernel-defined visual stimulus Λ is synthesized by multiplying the resynthesized bandwidth-limited visual stimulus (input signal) by the recomputed Wiener kernel representation of the system in an array processor 56. The optimal kernel-defined visual stimulus Λ may be defined for each of the channels or electrodes of the formula $$\Lambda = \sum_0^n \{[h_1, h_2, h_3] f(I)\}$$

where $f(I)$ is the bandwidth-limited visual stimulus given by the equation $$f(I) = \sum_{r=r_1}^{r_n} \sum_{g=g_1}^{g_n} \sum_{b=b_1}^{b_n} (r, g, b)$$

where "$n$" equals the video frame number and "$r$", "$g$" and "$b$" represent the red, green and blue color guns of the video monitor respectively.

The output of the array processor will be the set of optimal kernel-defined visual stimulus signals (actually the digital representation thereof) and these signals may be supplied via data path 57 to an input of the color video monitor system 42 and used to generate an individual kernel-defined optimal visual stimulus Λ for each of the electrodes 36 under consideration. The optimal visual stimulus Λ will be displayed on the screen 35 and summed on the retina and associated neural network of the subject 33 whose brain is being examined. The responses will be measured by the electrodes 36, amplified in amplifier 39 and stored in storage media 45. The subject may be asked various questions such as whether or not he experiences an epileptic aura from any given optimal visual stimulus and his response can be compared with the electrical analog responses recorded on the storage media 45. Based on such questions, neurophysiologically significant responses coupled with the known location of those electrodes whose Λ-defined visual stimuli produced those significant responses and the nature thereof, we can proceed to specifically isolate the anatomical location of the dysfunction.

The output from the array processor 56 and/or the CPU 48 may be taken from the bus 53 and supplied via data path 58 to an output recorder 59 which may, for example, by a typical prior art strip recorder, an oscilloscope or the like.

The present invention also contemplates the use of a standard electrical spike and slow potential waveform indicative of epilepsy which can be recorded in the storage media 35 or in the memory of the CPU 48. The broadband electrical analog waveforms from the electrodes 36 of the subject's brain which were initially amplified and stored can be cross-correlated with the stored representation of the standard waveform to identify specific known epilepti electrical spike and slow potential activity.

Additionally, a psychophysical test may be given the subject utilizing the optimal Weiner kernel-defined stimuli Λ which were previously synthesized. The subject would be shown two visual stimuli and asked to make a judgement "same" versus "different" for the conditions $f_1(I) + f_2(I)$ vs. $f_1(I) + \Lambda$ for bilaterally equivalent electrode placements. In this equation, "$f_1(I)$" represents the broadband noise-like visual stimuli and "$f_2(I)$" represents the bandwidth-limited stimuli. The responses would be plotted as a conventional signal detection task and sorted according to criterion levels. Criterion changes represent shifts in the slow DC potentials, for example, reticular activating formation shifts or drug-induced synaptic modulation shifts.

Given a group of behavioral trials of constant criterion, one can recompute the power spectrum of the short epochs and then reconstruct noise trials from the signal trials with the residue indicating function or dysfunction, as experienced is gained for particular stimulus-brain area combinations. While this may appear to be an extremely time-consuming task, the use of the bandwidth-limited visual stimulus and the fact that only the optimal visual stimulus for each placed electrode is used, renders it feasible. The study of the results of such tests will generate additional neurophysiologically meaningful information and will greatly aid in obtaining an understanding of the cognitive processes which are presently not fully understood. The measurements will also have great theoretical significance due to the ability to continuously monitor direct-coupled offset potentials without the sacrifice of information pertaining to spike and slow potentials.

With this detailed description of the apparatus used to illustrate the prime embodiment of the system and the method of the present invention, it will be obvious to those skilled in the art that various modifications can be made in the present apparatus of the system and in the various steps of the method and that various alternative embodiments can be utilized. Furthermore, it will be recognized that the broad concept of the method of the present invention finds application in examining other areas of the brain for other syndromes and is not limited to the human visual sensory system. Therefore, it will be recognized that various modifications can be made in both the method and apparatus of the present invention and in the applications to which the method and system are applied without departing from the spirit and scope of the invention which is limited only by the appended claims.

I claim:

1. A method for determining the specific anatomical localization of dysfunction in temporal lobe epilepsy comprising the steps of:

placing a plurality of electrodes with respect to physical areas of the subject's brain;

generating a pseudorandom, repeatable, broadband visual stimulus;

summing the broadband visual stimulus on the retina and associated neural networks of the subject;

amplifying the electrical analog response signal measured by each of the placed electrodes;

recording the amplified analog response signal from each electrode;

resynthesizing the broadband visual stimulus;

cross-correlating the resynthesized broadband visual stimulus with the recorded analog response signal for each placed electrode to obtain at least a first, second and third order Wiener kernel representation thereof;

limiting the bandwidth of the visual stimulus by masking out those portions which produce non-significant electrical analog responses;

summing the bandwidth-limited visual stimulus on the retina and associated networks of the subject;

amplifying the bandwidth-limited electrical analog response signal measured by each of the placed electrodes;

recording the amplified bandwidth-limited electrical analog response signals from each electrode;

resynthesizing the bandwidth-limited visual stimulus;

cross-correlating the resynthesized bandwidth-limited visual stimulus with the stored bandwidth-limited analog response signal for each electrode to recompute at least a first, second and third order Wiener kernel representation thereof;

synthesizing an optimal kernel-defined visual stimulus Λ for each of said electrodes by multiplying the resynthesized bandwidth-limited visual stimulus by the recomputed Wiener kernel representation of the system;

presenting an optimal Λ-defined visual stimulus to the subject for each placed electrode;

summing the Λ-defined visual stimulus on the retina and associated neural network of the subject;

determining which of the Λ-defined visual stimuli produced neurophysiologically significant responses in the subject; and utilizing the known locations of those placed electrodes whose Λ-defined visual stimuli produced said significant responses and the nature thereof to specifically isolate the anatomical location of the dysfunction.

2. The method for determining the specific anatomical localization of dysfunction in temporal lobe epilepsy of claim 1 wherein said step of placing a plurality of electrodes includes arranging scalp electrodes about the surface of the subject's head.

3. The method for determining the specific anatomical localization of dysfunction in temporal lobe epilepsy of claim 1 wherein said step of placing a plurality of electrodes includes surfically implanting electrodes at different discrete physical locations within that section of the subject's brain to be examined.

4. The method for determining the specific anatomical localization of dysfunction in temporal lobe epilepsy of claim 1 wherein the step of generating a pseudorandon, repeatable, broadband visual stimulus includes:

arranging a concantenation of a series of shift registers to generate an endless pseudorandom sequence of binary digits;

utilizing a hierarchial network to pick off a given sequence thereof; and inputting the given pseudorandom sequence into a digital color video monitor for producing, on a television screen portion thereof, a broadband visual stimulus $f(I)$ defined by the equation $$f_n(I) = \sum_{r=r_1}^{r_n} \sum_{g=g_1}^{g_n} \sum_{b=b_1}^{b_n} (r,g,b)$$

where "$n$" equals the video frame number and where "$r$", "$g$", and "$b$" represent the red, green and blue color guns of the video monitor.

5. The method for determining the specific anatomical localization of dysfunction in temporal lobe epilepsy of claim 1 wherein said step of amplifying the electrical analog response signal measured by each of the placed electrodes includes providing a very high-impedance amplifier having very low amplifier noise and a plurality of channels, at least one amplifying channel for each of said placed electrodes, said amplifier being capable of receiving and amplifying both spike and slow potential electrical analog response waveforms from the subject's brain.

6. The method for determining the specific anatomical localization of dysfunction in temporal lobe epilepsy of claim 5 wherein said amplifying step further includes providing said amplifier with a DC offset input responsive to a compensation signal to allow amplifier compensation for large potential variences while maintaining high input impedance and low amplifier noise, monitoring for great changes in the potential produced at said electrodes, generating a digitally controlled compensation signal in response thereto and feeding said compensation signal to said DC offset input for compensation purposes.

7. The method for determining the specific anatomical localization of dysfunction in temporal lobe epilepsy of claim 1 wherein said step of recording the amplified analog response signal for each electrode includes storing said analog response signal on magnetic tape having one-channel for each of said placed electrodes.

8. The method for determining the specific anatomical localization of dysfunction in temporal lobe epilepsy of claim 1 wherein said step of resynthesizing the broadband visual stimulus includes the step of regenerating said pseudorandom repeatable broadband visual stimulus.

9. The method for determining the specific anatomical localization of dysfunction in temporal lobe epilepsy of claim 1 wherein said step of generating a pseudorandom repeatable broadband visual stimulus is followed by the step of storing a representation of said generated pseudorandom repeatable broadband visual stimulus and wherein said step of resynthesizing includes playing back said stored representation of said generated pseudorandom repeatable broadband visual stimulus.

10. The method for determining the specific anatomical localization of dysfunction in temporal lobe epilepsy of claim 9 wherein said step of cross-correlating includes:

determining a first time lag $\sigma_1$;

cross-correlating to compute a first order Wiener kernel $h_1$ where $$h_1(\sigma_1) = \frac{1}{k} \overline{y(t)y_1(t)}$$

for $$\phi_{xx}(w) = \frac{k}{2\pi}$$

where $\phi_{xx}$ is an autocorrelation function and where $y(t)$ is the electrical analog response signal from the brain while $y_1(t)$ represents a delayed representation of the visual stimulus f(I);

determining a second time lag $\sigma_2$;

cross-correlating to compute a second order Wiener kernel $h_2$ where $$h_2(\sigma_1,\sigma_2) = \frac{1}{2k^2} \overline{y(t)y_2(t)}$$

determining a third time lag $\sigma_3$;

cross-correlating to compute a third order Wiener kernel $h_3$ where $$h_3(\sigma_1,\sigma_2,\sigma_3) = \frac{1}{6k^3} \overline{y(t)y_3(t)}$$

for $\sigma_1 \neq \sigma_2 \neq \sigma_3$ and summing the various order kernels to construct a kernel-defined response for each of said placed electrodes.

11. The method for determining the specific anatomical localization of dysfunction in temporal lobe epilepsy of claim 10 wherein said step of cross-correlating further includes the step of computing the $n$th order Wiener kernel by determining the time lag $\sigma_n$ and then cross-correlating to compute an $n$th order Wiener kernel $h_n$ where $$h_n(\sigma_1,\sigma_2,\ldots\sigma_n) = \frac{1}{n!k^n} \overline{y(t)y_n(t)}$$

except where for $n > 2$, two or more $\sigma$'s are equal.

12. The method for determining the specific anatomical localization of dysfunction in temporal lobe epilepsy of claim 1 wherein the step of limiting the bandwidth of the visual stimulus includes determining insignificant cross-correlation products whose absolute values are approximately zero and preventing the generation of those portions of the generated pseudorandom visual stimulus giving rise to those responses whose cross-correlation products are determined to be insignificant thereby limiting the bandwidth of said visual stimulus.

13. The method for determining the specific anatomical localization of dysfunction in temporal lobe epilepsy of claim 4 wherein the step of limiting the bandwidth of the visual stimulus includes the step of determining insignificant cross-correlation products whose absolute values are approximately zero, determining which sequences of binary digits from the total generated pseudorandom sequence of binary digits resulted in said insignificant cross-correlation products and masking out the generation of those determined sequences of binary digits from said generated pseudorandom sequence of binary digits to limit the bandwidth of said visual stimulus.

14. The method for determining the specific anatomical localization of dysfunction in temporal lobe epilepsy of claim 1 wherein each step of synthesizing an optimal kernel-defined visual stimulus Λ for each of said electrodes includes inputting the bandwidth-limited visual stimulus and the recomputed Wiener kernel representation of the response into a high speed array processor, multiplying the bandwidth limited visual stimulus by the Wiener kernel representation of the response and summing the output to form an optimal kernel-defined visual stimulus Λ for each placed electrode where $$\Lambda = \sum_0^n [(h_1, h_2, h_3) f(I)]$$

where $h_1$, $h_2$, and $h_3$ represent the first, second and third recomputed Wiener kernel representations of the response signal and $f(I)$ represents the bandwidth-limited visual stimulus.

15. The method for determining the specific anatomical localization of dysfunction in temporal lobe epilepsy of claim 1 wherein said step of presenting an optimal Λ-defined visual stimulus to the subject for each placed electrode includes feeding the kernal-defined optimal visual stimulus into a digital color video monitor and generating a color video representation thereof for observation by said subject.

16. The method for determining the specific anatomical localization of dysfunction in temporal lobe epilepsy of claim 1 further including the steps of storing a standard spike and slow potential waveform indicative of epilepsy; playing out the stored standard waveform and the recorded broadband analog response signal; and cross-correlating the stored representation of the standard waveform with the recorded broadband analog response signal to identify epileptic spike and wave activity.

17. The method for determining the specific anatomical localization of dysfunction in temporal lobe epilepsy of claim 1 further including the additional step of constructing a meaningful psychophysical test utilizing the optimal Wiener kernel-defined stimuli Λ wherein the subject is required to make a judgement "same" versus "different" for the condition $f_1(I) = f_2(I)$ vs $f_1(I) + \Lambda$ for bilaterally equivalent electrode placements and plotting the responses as a signal detection task for sorting according to criterion levels such that when noise trials are subtracted from signal trials, the residue will indicate function or dysfunction for particular stimulus-brain area combinations thereby generating additional neurophysiologically meaningful information.

18. A system for synthesizing a set of "$n$" discrete optimal visual stimuli, one optimal visual stimulus for each different and distinct brain area being examined, for use in determining the anatomical localization of brain dysfunction, said system comprising:

means for generating a pseudorandom input signal having the general characteristics of Gaussian white noise;

means responsive to said input signal for displaying a color video visual stimulus representation thereof, said visual stimulus being displayed so that it may be summed on the retina and associated neural network of the subject whose brain is being examined;

a plurality of "$n$" individual electrodes, one of said electrodes being disposed adjacent each of said different and distinct brain areas to be examined for monitoring the electrical spikes and slow potential response produced in said areas when said subject observes said displayed visual stimulus;

high impedance, low noise amplifier means having "$n$" channels, each of said channels being coupled to a different and distinct one of said "$n$" electrodes for amplifying the spikes and slow potential electrical analog response signals therefrom;

means for storing the amplified output of each of said "$n$" channels;

computational means responsive to said storage means and to said input signal-generating means for cross-correlating a resynthesized input signal with said stored electrical analog response signal for computing a Wiener kernel representation of the response from each of said electrodes for determining which portions of said input signal gave rise to insignificant responses;

means responsive to a determination of which portions of said input signal were responsible for insignificant responses for masking out the subsequent generation thereof so as to limit the bandwidth of any subsequently generated input signals;

said computational means being responsive to the resynthesized subsequently regenerated bandwidth-limited input signal and to the subsequently stored electrical analog response signals measured by said electrodes in response to the subject's observation of the displayed bandwidth-limited visual stimulus resulting from said bandwidth-limited input signal for cross-correlating to obtain a recomputed Wiener kernel representation of the output of each of said electrodes; and array processor means responsive to said recomputed Wiener kernel representation of the output of each of said electrodes and to the resynthesized bandwidth-limited input signals for multiplying same to produce an optimal input signal for each of "$n$" electrodes which can be supplied to said display means for displaying an optimal visual stimulus for testing each of said different and distinct brain areas being examined to anatomically localize brain dysfunction.

19. The apparatus of claim 18 wherein each of said plurality of "n" individual electrodes is a surface electrode adapted to be attached to the surface of the subject's head for testing the different and distinct brain area located thereunder.

20. The system of claim 18 wherein each of said plurality of the "n" individual electrodes is adapted to be surgically implanted within the different and distinct brain areas to be examined.

21. The system of claim 18 wherein said means for generating a pseudorandom input signal includes a concentration of a series of binay shift registers for generating an endless sequence of binary digits, a hierarchial-network adapted to pick off a given pseudorandom sequence from said endless sequence, and means for multiplexing binary digits from said given pseudorandom sequence into complete words capable of controlling said color video display to generate said visual stimulus.

22. The system of claim 18 wherein said amplifier means includes means responsive to large potential variants such as may be produced by electrical build-up at the electrode for generating a control signal, said amplifier means having a DC offset terminal responsive to the application of said control signal thereto to compensate for said large potential variants while maintaining a high input impedance and low amplifier noise for both spike and slow potential waveforms.

23. The system of claim 18 wherein said means for storing the amplified output of each of said "n" channels incudes a "n"-channel analog storage tape.

24. The system of claim 18 further including output means for recording both the broadband electrophysiological spike and slow potentials and the derived functions resulting from the cross-correlations for analysis purposes.

25. A method for determining the anatomical localization of dysfunction in the sensory systems of a brain under examination comprising the steps of:
placing a plurality of electrodes adjacent various distinct areas of the brain to be examined;
generating a sensory stimulus having the general characteristics of white noise;
exposing the subject whose brain is being examined to the generated sensory stimulus;
amplifying the electrical analog response signal measured by each of the placed electrodes;
recording the amplified analog response signal from each electrode;
resynthesizing the original sensory stimulus;
cross-correlating the resynthesized sensory stimulus with the recorded analog response signal for each placed electrode to obtain at least a first and second order Wiener kernel representation thereof;
limiting the bandwidth of the sensory stimulus by masking out those portions which tended to produce insignificant electrical analog responses in the brain of the subject under examination;
exposing the subject to a bandwidth-limited sensory stimulus;
amplifying the electrical analog response signal measured by each of the placed electrodes;
recording the amplified electrical analog response signals from each electrode;
resynthesizing the bandwidth-limited sensory stimulus;
cross-correlating the resynthesized, bandwidth-limited sensory stimulus with the stored bandwidth-limited analog response signal for each electrode to recompute at least a first and second order Wiener kernel representation thereof;
synthesizing an optimal kernel-defined visual stimulus for each of said electrodes by multiplying the resynthesized bandwidth-limited sensory stimulus by the recomputed Wiener kernel representation;
subsequently exposing the subject to the synthesized optimal kernel-defined sensory stimuli; and
utilizing the known locations of the placed electrodes whose optimal kernel-defined sensory stimuli produced significant neurophysiological responses in the subject to aid in determining the anatomical localization of dysfunction in the brain.

* * * * *